(12) United States Patent
Lyon et al.

(10) Patent No.: US 9,314,159 B2
(45) Date of Patent: Apr. 19, 2016

(54) PATIENT MONITORING DEVICE WITH REMOTE ALERT

(71) Applicant: Physio-Control, Inc., Redmond, WA (US)

(72) Inventors: Richard Mark Lyon, Edinburgh (GB); Robert G. Walker, Seattle, WA (US); Jeffery S. Edwards, Redmond, WA (US); Niklas Andersson, Seattle, WA (US); Bethany Joyce Johnson, Snoqualmie, WA (US)

(73) Assignee: Physio-Control, Inc., Redmond, WA (US)

( * ) Notice: Subject to any disclaimer, the term of this patent is extended or adjusted under 35 U.S.C. 154(b) by 123 days.

(21) Appl. No.: 14/035,903

(22) Filed: Sep. 24, 2013

(65) Prior Publication Data

US 2014/0085082 A1 Mar. 27, 2014

Related U.S. Application Data

(60) Provisional application No. 61/704,710, filed on Sep. 24, 2012.

(51) Int. Cl.
*G08B 1/08* (2006.01)
*A61B 5/00* (2006.01)
*A61B 5/0205* (2006.01)

(52) U.S. Cl.
CPC ............ *A61B 5/0004* (2013.01); *A61B 5/0002* (2013.01); *A61B 5/0205* (2013.01); *A61B 5/746* (2013.01); *A61B 5/7465* (2013.01)

(58) Field of Classification Search
CPC ............ A61B 1/00; A61B 3/00; A61B 5/00; A61B 5/0002; A61B 5/0004; A61B 5/0205; A61B 5/746; A61B 5/7465; H04W 24/00
See application file for complete search history.

(56) References Cited

U.S. PATENT DOCUMENTS

| | | | |
|---|---|---|---|
| 5,050,612 A * | 9/1991 | Matsumura | 600/483 |
| 5,400,301 A | 3/1995 | Rackley | |
| 6,560,165 B1 | 5/2003 | Barker | |
| 6,736,759 B1 * | 5/2004 | Stubbs et al. | 482/8 |
| 2003/0208110 A1 * | 11/2003 | Mault et al. | 600/300 |
| 2009/0076350 A1 * | 3/2009 | Bly | A61B 5/0006 600/301 |
| 2009/0243833 A1 * | 10/2009 | Huang et al. | 340/505 |
| 2010/0087900 A1 | 4/2010 | Flint | |
| 2011/0224505 A1 * | 9/2011 | Sadhu | 600/301 |
| 2011/0257544 A1 | 10/2011 | Kaasinen et al. | |
| 2012/0112903 A1 * | 5/2012 | Kaib et al. | 340/539.12 |
| 2012/0165688 A1 * | 6/2012 | Liu et al. | 600/500 |
| 2012/0203076 A1 * | 8/2012 | Fatta et al. | 600/300 |
| 2012/0203078 A1 * | 8/2012 | Sze et al. | 600/301 |
| 2012/0232366 A1 | 9/2012 | Kiani et al. | |
| 2012/0286955 A1 | 11/2012 | Welch et al. | |

* cited by examiner

*Primary Examiner* — Kerri McNally
*Assistant Examiner* — Renee Dorsey
(74) *Attorney, Agent, or Firm* — Marger Johnson

(57) ABSTRACT

A remote patient monitoring system provides patient physiological data and alerts/alarms from a main patient monitor to a remote patient monitor worn by a medical professional. The medical professional is alerted as to physiological data of the monitored patient, and provided alerts or alarms when predetermined levels are reached. The medical professional is able to reset the alert or alarms at the remote patient monitor.

20 Claims, 5 Drawing Sheets

PATIENT MONITORING DEVICE WITH REMOTE ALERT

RELATED APPLICATION

This application claims the benefit of priority of U.S. Provisional Patent Application Ser. No. 61/704,710 filed Sep. 24, 2012, the disclosure of which is hereby incorporated by reference for all purposes.

BACKGROUND

In typical medical care situations, monitors are connected to devices that receive physiological data from patients. Such devices may be passive monitoring devices or active delivery devices. Active delivery devices, for example, may provide stimulus (e.g., cardiopulmonary resuscitation (CPR) machines), drugs, and/or oxygen.

In such situations, the monitors of such devices provide critical patient information to the caregivers, such as health care providers or medical professionals (e.g., medical doctors, nurses, emergency medical technicians, etc.). In many cases, the monitors are connected to the devices as an integrated package. Oftentimes, the monitors are not readily visible to the caregivers, particularly if the caregivers are away from the patient and the devices.

Although caregivers are away from the monitors and devices, the need to be aware of a patient's condition(s) continues. In certain cases, a medical professional may not be able to view a monitor and be aware of the patient's condition(s). Examples of such situations, include instances when the caregiver has to walk away to check on another patient or attend to another task. In certain cases, a caregiver is physically unable to view a monitor. An example includes a medical evacuation situation in a helicopter when a technician and patient are physically situated such that the technician is unable to view the monitor of the device. Furthermore, in such medical evacuation situations, the environment may not be ideal (e.g., noisy, dimly lit, etc.) to properly view the monitor.

In certain situations, a monitor not only provides status of physiological data and of the connected device, but may also provide alerts as to critical levels of a patient. For example, a blood pressure device may alert the medical professional as to a critically low blood pressure level and/or irregular heartbeat. In the case of an oxygen sensing device, a monitor may alert the professional as to low levels of oxygen to the patient. Such alerts may be triggered by abnormalities/conditions experienced by the patient and/or problems/malfunctions of the device.

If a caregiver is away from a monitor, the patient's care may be compromised because the caregiver cannot properly view the condition of the patient or be aware of alerts provided by the device through the monitor.

BRIEF SUMMARY

The present description gives instances of medical technology that facilitates the remote monitoring of patients.

In one embodiment, a medical device facilitates monitoring of a patient. The medical system includes a main patient monitor collecting patient physiological parameter data, and also capable of transmitting the collected patient physiological parameter data. The main patient monitor alarms if the collected data is determined to reach a predetermined value. The device further includes a remote patient monitor, also referred to as a remote patient monitoring device, in the form of a wrist band, worn by a caregiver, configured to receive the collected patient physiological parameter data, display the collected patient physiological parameter data received from the main patient monitor, and receive a signal in response to an alarm(s) from the main patient monitor.

In one embodiment, the remote patient monitor can be a bracelet, a wrist or arm band, or other type of a small, compact, or wearable device. The remote patient monitor interfaces with the main patient monitor, a defibrillator, and/or other medical device or system. Alternatively, the remote patient monitor operates as a stand-alone, such as a puck or is incorporated into another device, such as a cell phone, a watch, bag valve mask, defibrillation electrodes, etc. The remote patient monitor allows a wearer of the device to monitor a patient through pre-set alarms, which can manifest as one or a combination of visual, tactile, auditory types of notifications, which may vary in intensity and duration depending on the preset parameters.

In some embodiments, the remote patient monitor includes a sensory feedback, such as haptic feedback, guiding a rescuer, dictating the rate via metronome, and/or notifying of elapsed time in Cardiopulmonary Resuscitation (CPR). The remote patient monitor further may include haptic feedback mechanism in bag valve mask (BVM). The remote patient monitor is, in one example, configured to differentiate haptic sensation to the wearer/rescuer to signify that a two-minute cycle has elapsed, and further to detect ventricular fibrillation (VF) or shockable rhythm, ST-elevation, ROSC (Return of Spontaneous Circulation), apnea, desaturation, etc. These and other features and advantages of this description will become more readily apparent from the following Detailed Description, which proceeds with reference to the drawings, in which:

DETAILED DESCRIPTION

As has been mentioned, the present description pertains to remote patient monitoring technology. Embodiments are now described in more detail.

Patient Monitoring System

Figure 1:
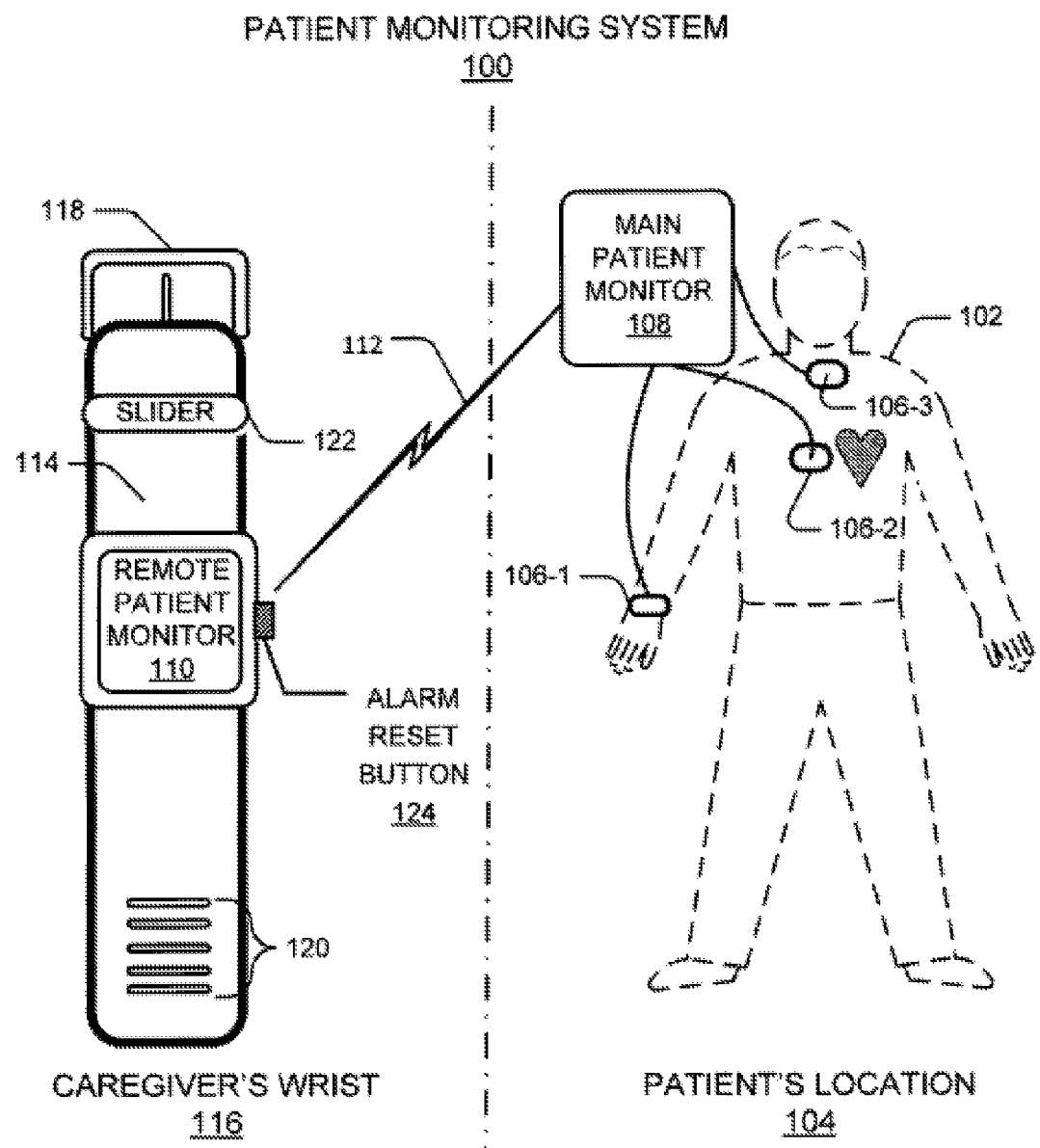
FIG. 1 is a diagram of a remote patient monitoring system used to remotely provide physiological data and alerts of a patient according to one or more embodiments described herein.

FIG. 1 is a diagram of a remote patient monitoring system 100 according to the technology described herein. A patient 102 may be in particular location 104. A patient may be, by way of example, a hospital patient in bed in a particular unit with more less stationary devices and monitors around his/her bed or may be an ambulatory or outside-a-hospital patient accessorized with devices such as implantable devices or monitoring and therapy devices attached to the patient. In certain instances, a caregiver (not shown) may be in a different location. Various medical probes and/or delivery devices 106 are connected to the patient 102. A main patient monitor 108 is connected to medical probes and/or delivery devices 106. The medical probes and/or delivery devices 106 may actively provide medicine, oxygen and/or liquids to the patient 102. In some embodiments, the medical probes and/or delivery devices 106 monitor and/or track physiological parameter data. The physiological parameter data may include one or more vital signs. For example, physiological parameter data may include heart rate, blood pressure, oxygen saturation, end-tidal CO2, respiration rate level of the monitored patient 102.

The main patient monitor 108 may be configured to collect patient physiological parameter data, to transmit the collected patient physiological parameter data, and to alarm if the collected data is determined to reach a predetermined value. Other alarms may be provided, such as condition states of the main patient monitor 108 and/or devices connected to the patient of the main patient monitor 108. Examples of condition states include low power/battery of the patient monitor 108 and/or devices, transmission connectivity to the remote patient monitor 110 and other networks, etc.

The main patient monitor 108 may be connected to a remote patient monitor 110. The connection between the main patient monitor 108 and the remote patient monitor 110 may be a wired or wireless connection as represented by connection 112. In other words, the main patient monitor 108 and the remote patient monitor 110 may be wired or wirelessly coupled to one another.

In certain embodiments, the main patient monitor 108 and remote patient monitor 110 may be connected intermediately through a network, such as a cloud based network. In other words, the connection 112 may go through or be part of a network or networks, which may include cloud based network(s). In certain embodiments, cloud based network(s) may perform monitoring based on information received from the main patient monitor 108.

The remote patient monitor 110 may be configured as or be part of a cell phone, puck, or arm or wrist band 114, that may be worn or carried by a caregiver, for example on a caregiver's wrist 116. In another embodiment, the band 114 may be a in a form of a necklace, arm band, or waist band, or other wearable device. Other embodiments are possible. Caregivers may include laypeople such as family members, and/or a trained medical professionals such as medical doctors, medical directors, nurses, emergency medical technicians (EMTs), and the like. Therefore in some embodiments, the remote patient monitor 110 may be in the form of a band, such as a wrist band 114 and configured to be worn by a caregiver, to receive the collected patient physiological parameter data. The remote patient monitor 110 further may display the collected patient physiological parameter data received from the main patient monitor 108, and to receive a signal in response to an alarm from the main patient monitor 108.

In some embodiments, the band 114 may be adjustable and may include a buckle 118 and holes to attach the buckle 118 to adjust to accommodate for various sized wrists, waists, etc. A slider 122 may be used to secure to excess length of the band 114. In addition to being adjustable, the band 114 may also be waterproof and/or shock-resistant. In certain embodiments, the band 114 may be in the form of or attached to a necklace or lanyard around the caregiver's neck. In other embodiments the band 114 may be in the form of or attached to a belt around the caregiver's waist. Other embodiments may provide for the remote patient monitor 110 to be clipped onto the caregiver's clothing, such as on a lapel or chest pocket. Other embodiments may provide for the remote patient monitor 110 to be implemented as a wearable device.

The remote patient monitor 110 may include an alarm reset button 124 to reset any alarms received from the main patient monitor 108. In certain embodiments, the alarm(s) that is(are) received by the remote patient monitor 110 include one or more of vibrate (e.g., tactile/haptic alarm), light up, and/or an audible noise. In particular embodiments, the remote patient monitor 110 only vibrates as determined by the main patient monitor 108.

In certain embodiments, the remote patient monitor 110 receives haptic/sensory feedback for patient monitoring that may include a guide rate for chest compression, such as used in CPR. In such an implementation, a patient may have a physiologic monitoring sensor, which is not necessarily "wearable", but merely attached to the patient. The patient sensor provides data to the remote patient monitor 110. The remote patient monitor 110 may include a haptic motor that conveys information to the caregiver in the form of "mimicked" sensory feedback from the patient. In yet certain other embodiments, monitoring data transmitted to the remote patient monitor 110 may be include information about ventilation (e.g. rate, tidal volume, airway pressure) being provided to the patient. The patient sensors may be incorporated as a wearable device (e.g., wrist band, head band, bracelet, etc.), standalone sensor, or incorporated into another device (e.g. bag valve mask).

In certain embodiments, the patient may be provided with disposable components such as a sticker with a wireless identifier (i.e., an RFID chip) to initiate or inform as to a haptic component/feedback. Different variations of such disposable components may make use of color coded stickers with RFID used to set various rates (e.g., 100/min for chest compression and 8/min for ventilation). Other colors may be used for various rate guidance purposes. Disposable component/sticker or RFIDs may be used to start or stop a patient/caregiver haptic motor when patient/caregiver is in proximity of the RFID. In certain implementation, a disposable component/sticker may be incorporated into a device, such as a defibrillator.

Other haptic signals may include use of different frequencies, duty cycles, sensations (vibration, taps, squeeze, etc.) to communicate different information. Physiological feedback could provide input signal to vibration intensity, rate, sensation, etc. The remote patient monitor 110 and particularly a wearable portion may incorporate a display, such that a haptic signal would alert the caregiver and the display would provide detailed information about the alert.

In certain embodiments, depending on the level of a caregiver's expertise, the alarm(s) that is(are) received by the remote patient monitor 110 may be activated based on specific preset threshold values. The alarms may include a general overall urgency alarm, and/or specific alarms. Variety of settings may be determined depending on the patient's condition, parameters, status and combined with the caregiver's rank, skills, expertise, and preferences. An alarm may be initiated at the remote patient monitor 110 to indicate an urgent need to respond to the patient, such as a cardiac arrest, an oxygen desaturation, etc. In such cases, a general urgency alarm may be activated, and/or specific alarms indicating specific medical conditions may be activated. Specific alarms may further be selected by a user/caregiver to differentiate between sounds, vibration patterns, and intensity depending on the patient identification, location, and other parameters. If several caregivers receive alarms pertaining to the same patient, and one of the alerted caregivers responds, other caregivers may be notified that the patient is being attended to. If the attending to the patient caregiver still needs additional help, the caregiver may be able to send another alarm to solicit further help. Alternatively, upon arrival at the patient's side or resolution as to the patient needs, one caregiver may terminate alarms sent to others and may further be able to follow up with a message as to the resolution of the issue.

Alarms may be sent by signals from the main patient monitor 108 to the remote patient monitor 110. After a period of time the signals may be degraded. Therefore, in certain embodiments a decoupling or a disconnection may occur between the main patient monitor 108 and the remote patient monitor 110 after a determined time period after a signal(s) is degraded. In certain instances it may be desirable for a caregiver to reset the alarm(s) of the remote patient monitor 110. An alarm reset button 124 is provided by the remote patient monitor 110 to allow resetting of the alarm(s).

The patient monitor 110, or a wearable portion of the patient monitor 110, may include a start/stop haptic feedback metronome which may include different pre-selected metronome rates such as ventilation (e.g., 8/min), compression (e.g., 100/min), etc.

In certain embodiments, the remote patient monitor 110 may be coupled to more than one main patient monitors, including the main patient monitor 108 that is shown. In such embodiments, the remote patient monitor 110 is configured to receive various patient physiological parameter data and alarms from different medical devices and/or patients.

In certain embodiments, there may be more than one patient. Therefore, the remote patient monitor 110 may be coupled to more than one main patient monitors and/or one or more patients.

The patient monitoring system 100 may be part of different health care environments. In certain embodiments, the patient monitoring system 100 may be part of a hospital environment that includes nursing stations. A nursing station may include multiple patient monitors, such as main patient monitor 108.

Caregivers, such as medical doctors, nurses, etc., are able to simultaneously monitor patients from a central station at the nursing station. However, in certain situations the caregiver may be away from the central stations and the monitors, but would still need to be aware of the patients. In such cases, the remote patient monitor 110 may be configured to provide alarms to let the caregiver know the status of the patients and/or determine which patient(s) need to be attended to. In certain embodiments, the remote patient monitor 110 may provide a patient's name, room number (location) and/or other specific patient information. In certain embodiments, either through preset thresholds that are set at particular main patient monitor(s) 108, patients may be listed in order of need for medical attention or listed some other order, such as first request. In a further embodiment, the remote patient monitor is configured to monitor more than one patient simultaneously. If one caregiver is monitoring more than one patient, the remote patient monitor 110 can provide ranking of urgency between patients, depending on a patient's symptoms.

In certain embodiments, there may be multiple caregivers connected to the patient monitoring system 100. Provision may be made to allow a caregiver that is the first responder to the patient, to notify other caregivers that the first responding caregiver has reached the patient. Provision may also be provided to allow the first responding caregiver to request for additional help if needed. This may be performed through the remote patient monitor that is worn by the first responding caregiver.

In certain embodiments, the main patient monitor 108 may be configured with a cellular, global positioning system (GPS), or other tracking unit (not shown). The tracking unit may provide specific location of the patient (i.e., patient location 104). This may assist in identifying specific location of an ambulatory patient, to the remote patient monitor 110. The foregoing indications and responses described in conjunction with FIG. 1 can be implemented in various combinations in other embodiments, with each indication and/or response providing its advantages even if combined with other indication(s) and/or response(s).

Example Patient Monitoring System Components

Figure 2:
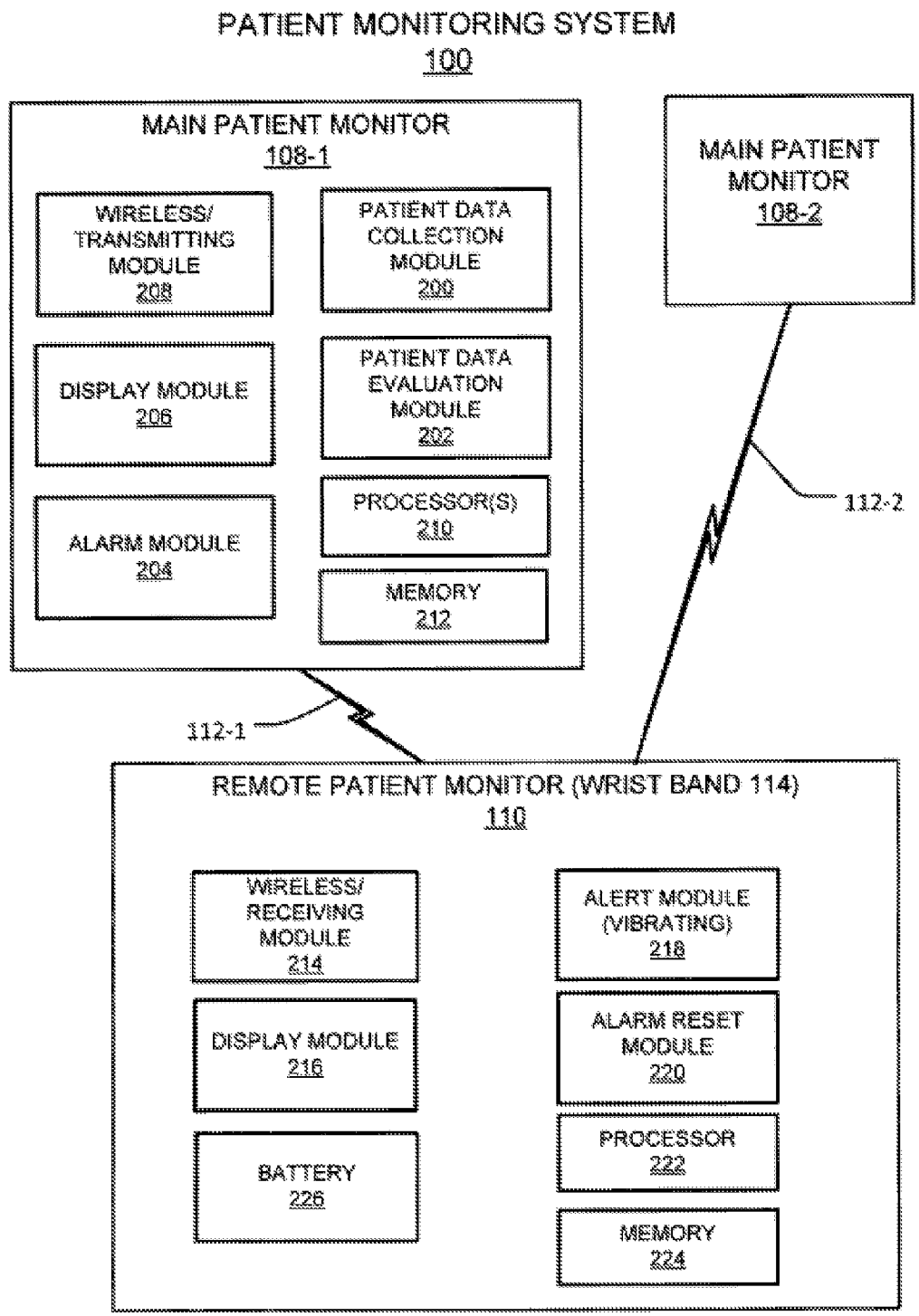
FIG. 2 is a diagram of a sample of a remote patient monitoring system used to remotely provide physiological data and alerts of a patient according to one or more embodiments described herein.

FIG. 2 is a diagram of a sample structure of a remote patient monitoring system 100 used to remotely provide physiological data and alerts of a patient according to the technology described herein. In the illustrated embodiment, one or more main patient monitors 108 are wire or wirelessly coupled to a remote patient monitor 110 by wire and/or wireless connections 112.

In this embodiment, a main patient monitor 108-1 is shown to include a patient data collection module 200 which communicates with and receives patient physiological data from one or more medical devices and/or probes, such as medical probes and/or delivery devices 106 described above. In particular, the patient data collection module 200 gathers patient physiological parameter data, which may include one or more vital signs of a monitored patient (e.g., patient 102). As an example, the patient physiological parameter data may particularly include one or more of the following: blood pressure, heart rate, respiration rate, pulse rate, oxygen saturation, air flow, temperature, ECG parameters, and/or other parameters. Device data, such as low battery on one of the devices/probes interfacing/interacting with the patient or the band's inability to access information, or other parameters/data, can also be included. Other example data that may be sent can include 1) physiologic data, such as vital signs data, and/or alarm info on vital signs excursions out of normal/stable ranges; 2) monitoring device data, battery status, sensor status, etc. (i.e., information meriting the attention or intervention of a caregiver); and 3) Medical care/intervention data, i.e., information about the presence or quality of the care being applied to the patient by someone other than the person wearing the remote patient monitor, for example, alert the person managing a resuscitation (and e.g. wearing a haptic wristband) that the person managing the airway is ventilating too fast, or the person doing chest compressions has paused for too long.

The main patient monitor 108-1 may include a patient data evaluation module 202 which is configured with values for patient physiological parameter data. Such values may be preset by a caregiver to trigger an alarm. For example, if a particular value reaches or exceeds a particular level or levels, the alarm or alarms may be triggered. In this example, an alarm module 204 may be configured to provide such alert(s) in response to reaching a predetermined value(s) for the patient physiological parameter data. Alarms or alerts may initiate one or more actions such as vibration, light up, or a noise/audible sound. Such alarms or alerts may be communicated to the remote patient monitor 110.

The main patient monitor 108-1 may include a display module 206 to display the patient physiological parameter data and/or alarms. A transmitting module 208 provides signals (e.g., one or more alarm signals) to the remote patient monitor 110. The signals to the remote patient monitor 110 may include the one or more actions such as vibration, light up, or a noise/audible/haptic sound/response. In certain embodiments, the transmitting module 208 is a wireless module that may implement one or more various wireless technologies, including but not limited to Bluetooth®, one or more the various IEEE 802.11 standards, etc.

The main patient monitor 108-1 includes one or more processors 210 couple with the other components of the main patient monitor 108-1. Volatile and nonvolatile memory 212 is included in main patient monitor 108-1. Memory 212 may include computer-readable storage medium that includes instructions to perform the acts/methods described herein.

The remote patient monitor 110 is wired or wireless coupled to the main patient monitors 108 by respective links or connections 112. The remote patient monitor 110 includes a receiving module 214. In certain embodiments the receiving module 214 is a wireless receiving module, which may implement one or more various wireless technologies, including but not limited to Bluetooth®, one or more the various IEEE 802.11 standards, etc. The receiving module 214 receives one more alerts, which may be in the form of one more transmitted signals from the main patient monitors 108. The received signals from main patient monitors 108 may include the one or more actions such as vibration, light up, or a noise/audible sound.

The remote patient monitor 110 may include display module 216 may display the patient physiological parameter data and/or alarms (alerts). The display module 216 may light up with a particular alert or alerts. The remote patient monitor 110 may include a separate alert module 218. A function the alert module may perform is to vibrate when a particular alert or alerts is/are received from the main patient monitors 108. An alarm reset module 220, which may be reset by alarm reset button 124 described above, may be implemented by the remote patient monitor 110 to reset one or more alerts and alarms that are activated/displayed.

The remote patient monitor 110 includes one or more processors 222 coupled with the other components of the remote patient monitor 110. Volatile and nonvolatile memory 224 is included in remote patient monitor 110. Memory 224 may include computer-readable storage medium that includes instructions to perform the acts/methods described herein. In certain embodiments, and particular where the remote patient monitor 110 is a portable unit, a long lasting battery(ies) 226 may be part of the remote patient monitor 110.

The foregoing indications and responses described in conjunction with FIG. 2 can be implemented in various combinations in other embodiments, with each indication and/or response providing its advantages even if combined with other indication(s) and/or response(s).

Example Physiological Data and Alerts

Figure 3:
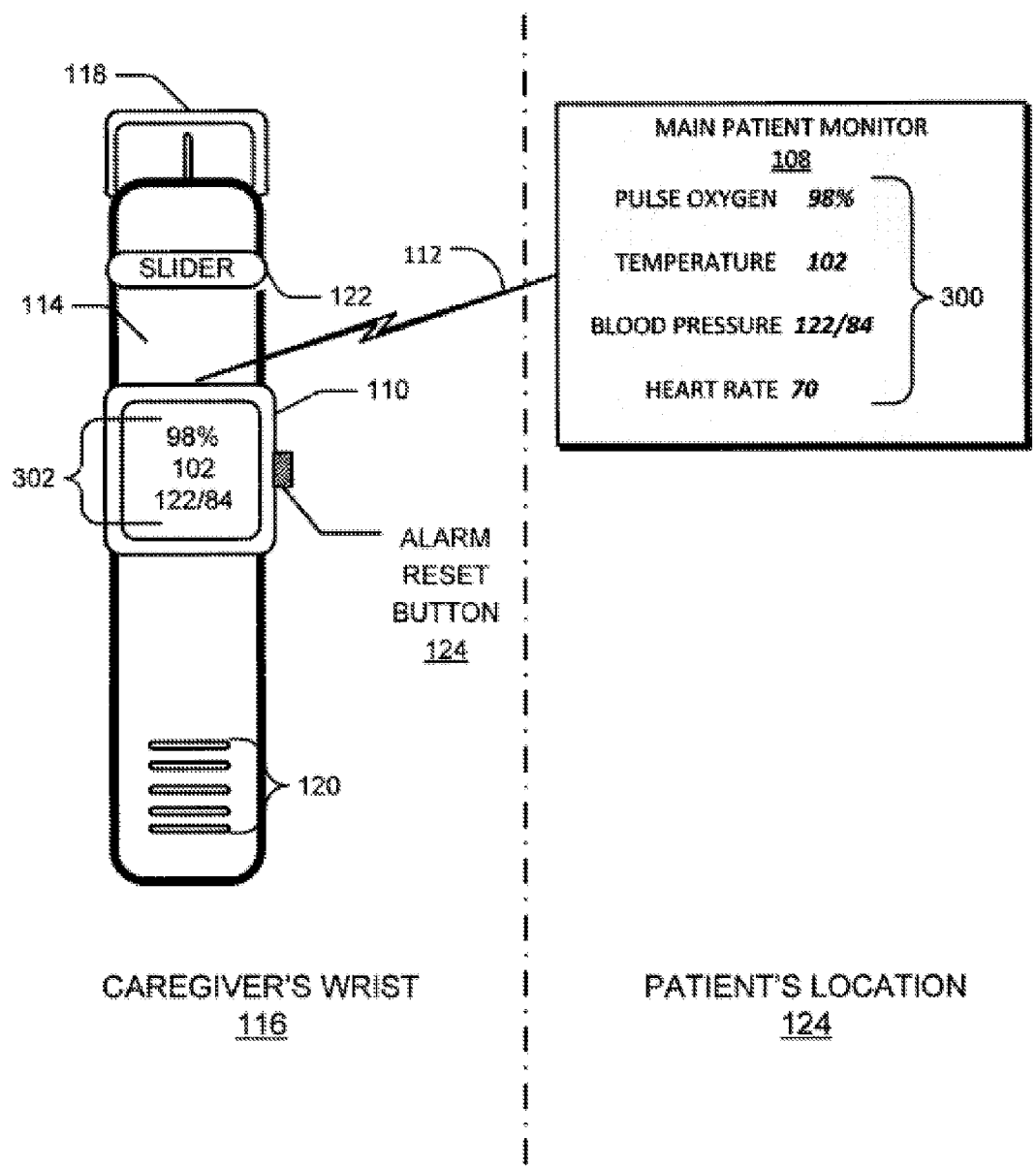
FIG. 3 is a diagram of sample physiological data and alerts that are remotely provided according to one or more embodiments described herein.

FIG. 3 is a diagram of sample physiological data and alerts that are remotely provided according to the technology described herein. The main patient monitor 108 may provide alarms/alerts of collected physiological data to the remote patient monitor 110. The physiological data may be for patient physiological parameter data. As described above, such patient physiological parameter data may have values that preset by a caregiver to trigger an alarm. For example, if a particular value reaches or exceeds a particular level or levels, the alarm or alarms may be triggered.

Shown in FIG. 3 are monitored physiological data 300 that includes current patient monitored values. In this example, pulse oxygen, temperature, blood pressure and heart rate values are monitored and displayed. Such values are communicated to the remote patient monitor 110 are displayed as patient physiological data 302. The displayed values shown in remote patient monitor 110 are a compact or condensed version displayed by the main patient monitor 108.

The functions of this description may be implemented by one or more devices that include logic circuitry. The device performs functions and/or methods as are described in this document. The logic circuitry may include a processor that may be programmable for a general purpose, or dedicated, such as microcontroller, a microprocessor, a Digital Signal Processor (DSP), etc. For example, the device may be a digital computer like device, such as a general-purpose computer selectively activated or reconfigured by a computer program stored in the computer. Alternately, the device may be implemented by an Application Specific Integrated Circuit (ASIC), etc.

Moreover, methods are described below. The methods and algorithms presented herein are not necessarily inherently associated with any particular computer or other apparatus. Rather, various general-purpose machines may be used with programs in accordance with the teachings herein, or it may prove more convenient to construct more specialized apparatus to perform the required method steps. The required structure for a variety of these machines will become apparent from this description.

In all cases there should be borne in mind the distinction between methods in this description, and the method of operating a computing machine. This description relates both to methods in general, and also to steps for operating a computer and for processing electrical or other physical signals to generate other desired physical signals.

Programs are additionally included in this description, as are methods of operation of the programs. A program is generally defined as a group of steps leading to a desired result, due to their nature and their sequence. A program is usually advantageously implemented as a program for a computing machine, such as a general-purpose computer, a special purpose computer, a microprocessor, etc.

Storage media are additionally included in this description. Such media, individually or in combination with others, have stored thereon instructions of a program made according to the technology described herein. A storage medium according to the technology described herein is a computer-readable medium, such as a memory, and is read by the computing machine mentioned above.

Performing the steps or instructions of a program requires physical manipulations of physical quantities. Usually, though not necessarily, these quantities may be transferred, combined, compared, and otherwise manipulated or processed according to the instructions, and they may also be stored in a computer-readable medium. These quantities include, for example electrical, magnetic, and electromagnetic signals, and also states of matter that can be queried by such signals. It is convenient at times, principally for reasons of common usage, to refer to these quantities as bits, data bits, samples, values, symbols, characters, images, terms, numbers, or the like. It should be borne in mind, however, that all of these and similar terms are associated with the appropriate physical quantities, and that these terms are merely convenient labels applied to these physical quantities, individually or in groups.

This detailed description is presented largely in terms of flowcharts, display images, algorithms, and symbolic representations of operations of data bits within at least one computer readable medium, such as a memory. Indeed, such descriptions and representations are the type of convenient labels used by those skilled in programming and/or the data processing arts to effectively convey the substance of their work to others skilled in the art. A person skilled in the art of programming may use these descriptions to readily generate specific instructions for implementing a program according to the technology described herein.

Often, for the sake of convenience only, it is preferred to implement and describe a program as various interconnected distinct software modules or features, individually and collectively also known as software. This is not necessary, however, and there may be cases where modules are equivalently aggregated into a single program with unclear boundaries. In any event, the software modules or features of this description may be implemented by themselves, or in combination with others. Even though it is said that the program may be stored in a computer-readable medium, it should be clear to a person skilled in the art that it need not be a single memory, or even a single machine. Various portions, modules or features of it may reside in separate memories, or even separate machines. The separate machines may be connected directly, or through a network, such as a local access network (LAN), or a global network, such as the Internet.

It will be appreciated that some of these methods may include software steps that may be performed by different modules of an overall software architecture. For example, data forwarding in a router may be performed in a data plane, which consults a local routing table. Collection of performance data may also be performed in a data plane. The performance data may be processed in a control plane, which accordingly may update the local routing table, in addition to neighboring ones. A person skilled in the art will discern which step is best performed in which plane.

An economy is achieved in the present document in that flowcharts are used to describe both programs, and also methods. So, while flowcharts are described in terms of boxes, they can mean both method and programs.

For this description, the methods may be implemented by machine operations. In other words, embodiments of programs are made such that they perform methods in accordance to embodiments of the technology that are described in this document. These may be optionally performed in conjunction with one or more human operators performing some, but not all of them. As per the above, the users need not be collocated with each other, but each only with a machine that houses a portion of the program. Alternately, some of these machines may operate automatically, without users and/or independently from each other.

Example Methods

Figure 4:
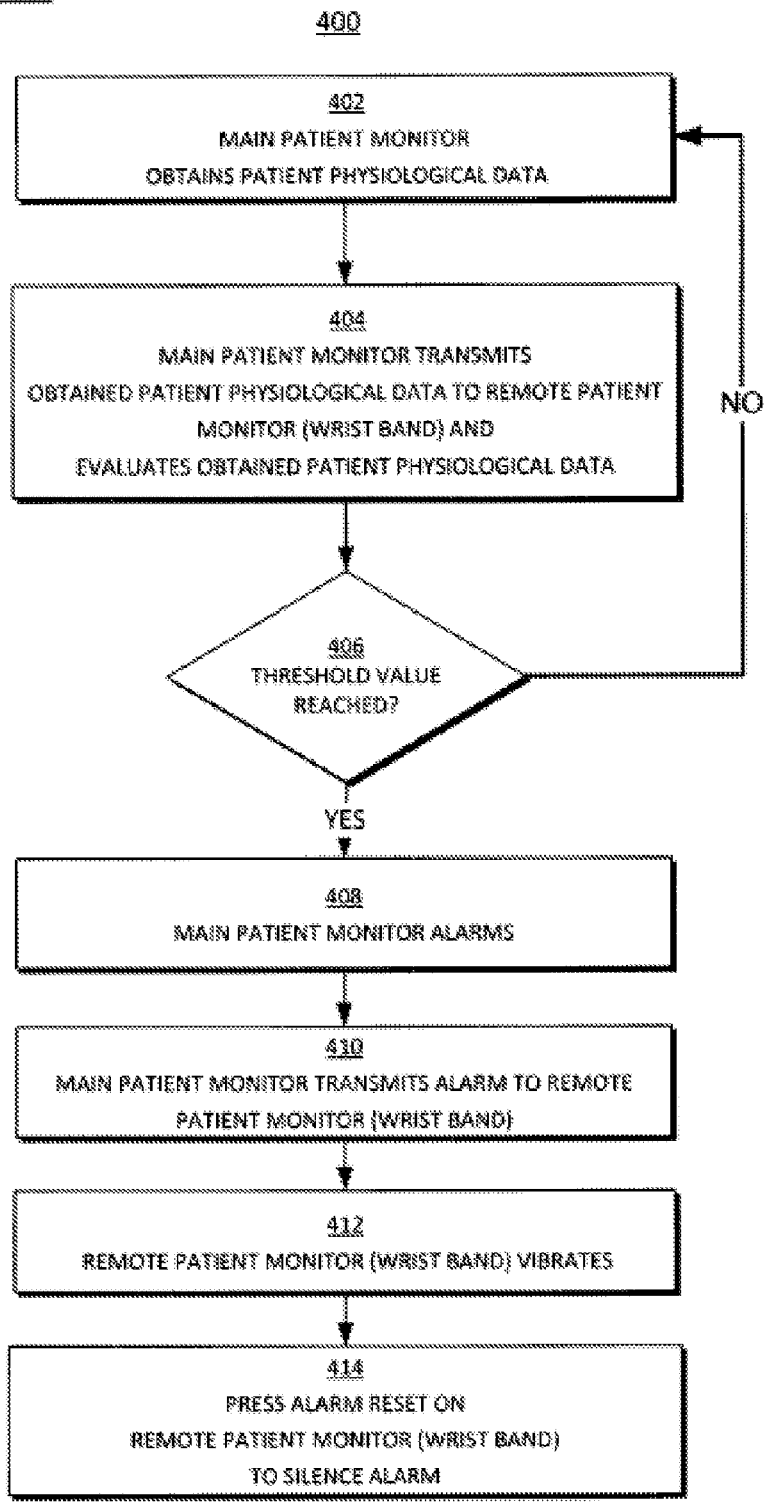
FIG. 4 is a flowchart for illustrating methods to remotely provide physiological data and alerts of a patient according to one or more embodiments described herein.

FIG. 4 shows a flowchart 400 for describing methods according to the technology described herein, for a patient monitoring system to remotely provide physiological data and alerts of a patient. The method of flowchart 400 may also be practiced by patient monitoring systems made according to the technology described herein described above.

According to an operation 402, a main patient monitor obtains patient's physiological data.

According to an operation 404, the main patient monitor transmits the obtained patient physiological data to a remote patient monitor, which may be part of or integrated as a wrist band, and the evaluates obtained patient physiological data.

According to an operation 406, a decision is made whether a threshold value is reached. If the threshold value is not reached, following the "NO" branch of operation 406, operation 402 is performed.

According to an operation 408, if the threshold value is reached as determined by operation 406, then following the "YES" branch of operation 406, the main patient monitor triggers or performs an alarm or alarms.

According to an operation 410, the main patient monitor transmits the alarm or alarms to the remote patient monitor.

According to an operation 412, the remote patient monitor vibrates, alerting a caregiver.

According to an operation 412, an alarm reset button on the remote patient monitor may be activated by the caregiver to silence the alarm or alarms.

For flowchart 400, it will be recognized that a number of their operations can be augmented with what was described above.

Figure 5:
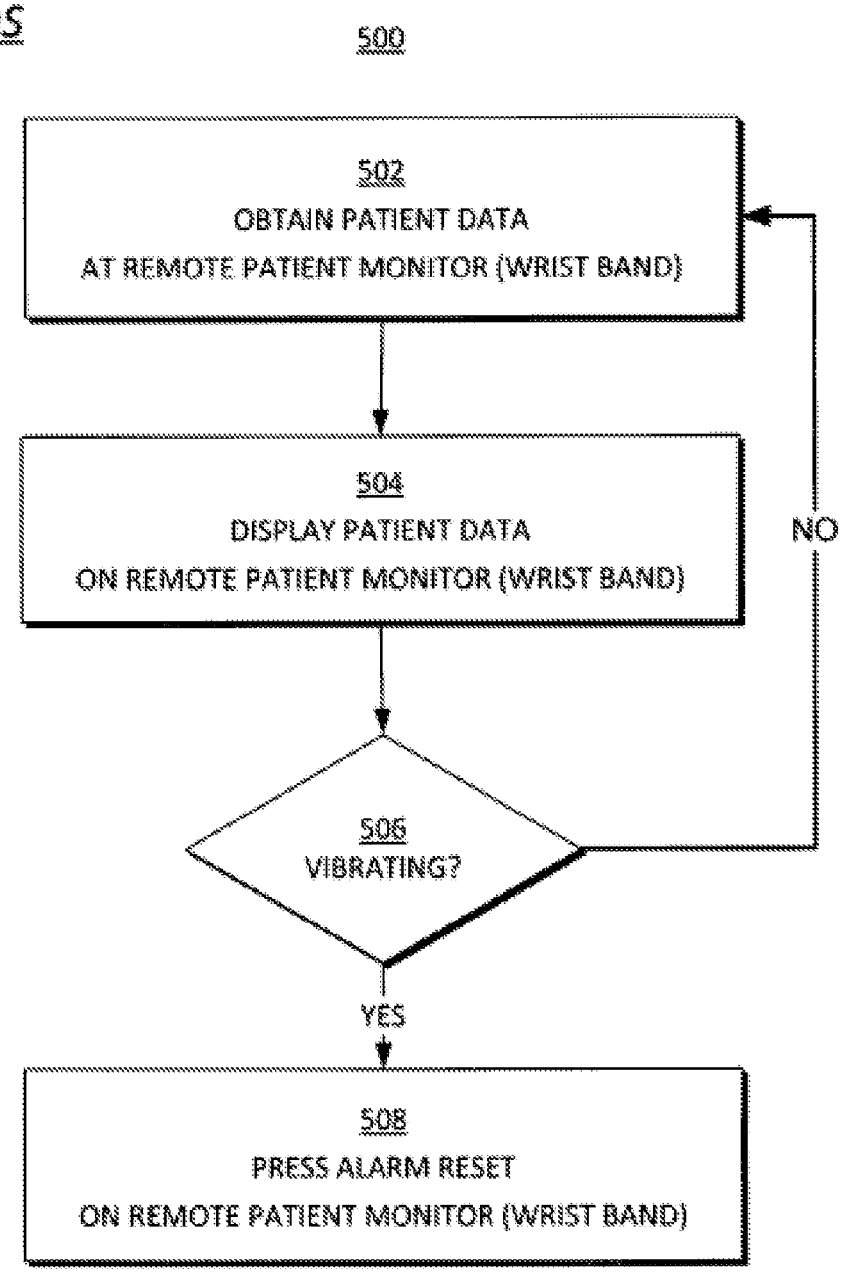
FIG. 5 is another flowchart for illustrating methods to remotely provide physiological data and alerts of a patient according to one or more embodiments described herein.

FIG. 5 is another flowchart 500 for describing methods according to the technology described herein, for a patient monitoring system to remotely provide physiological data and alerts of a patient. The method of flowchart 500 may also be practiced by patient monitoring systems made according to the technology described herein described above.

An operation 502 obtains patient physiological data at a remote patient monitor. The remote patient monitor may be part of or integrated as a wrist band.

An operation 502 displays the patient physiological data at the remote patient monitor.

An operation 506 determines if the remote patient monitor is vibrating. If the remote patient monitor is not vibrating, then following the "NO" branch of operation 506, operation 502 is performed.

According to an operation 508, if the remote patient monitor is vibrating as determined by operation 506, then following the "YES" branch of operation 506, the alarm or alarms on the remote patient monitor may be reset.

For flowchart 500, it will be recognized that a number of their operations can be augmented with what was described above.

Notes and Additional/Alternative Implementation Details

In the above description of exemplary implementations, for purposes of explanation, specific numbers, materials configurations, and other details are set forth in order to better explain the present invention, as claimed. However, it will be apparent to one skilled in the art that the claimed invention may be practiced using different details than the exemplary ones described herein. In other instances, well-known features are omitted or simplified to clarify the description of the exemplary implementations.

The inventor intends the described exemplary implementations to be primarily examples. The inventor does not intend these exemplary implementations to limit the scope of the appended claims. Rather, the inventor has contemplated that the claimed invention might also be embodied and implemented in other ways, in conjunction with other present or future technologies.

Moreover, the word "exemplary" is used herein to mean serving as an example, instance, or illustration. Any aspect or design described herein as exemplary is not necessarily to be construed as preferred or advantageous over other aspects or designs. Rather, use of the word "exemplary" is intended to present concepts and techniques in a concrete fashion. The term "technology," for instance, may refer to one or more devices, apparatuses, systems, methods, articles of manufacture, and/or computer-readable instructions as indicated by the context described herein.

As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

Note that the order in which the processes are described is not intended to be construed as a limitation, and any number of the described process blocks can be combined in any order to implement the processes or an alternate process. Additionally, individual blocks may be deleted from the processes without departing from the spirit and scope of the subject matter described herein.

One or more embodiments described herein may be implemented fully or partially in software and/or firmware. This software and/or firmware may take the form of instructions contained in or on a non-transitory computer-readable storage medium. Those instructions may then be read and executed by one or more processors to enable performance of the operations described herein. The instructions may be in any suitable form, such as but not limited to source code, compiled code, interpreted code, executable code, static code, dynamic code, and the like. Such a computer-readable medium may include any tangible non-transitory medium for storing information in a form readable by one or more computers, such as but not limited to read only memory (ROM); random access memory (RAM); magnetic disk storage media; optical storage media; a flash memory, etc.

The term "computer-readable media" includes computer-storage media. For example, computer-storage media may include, but are not limited to, magnetic storage devices (e.g., hard disk, floppy disk, and magnetic strips), optical disks (e.g., compact disk [CD] and digital versatile disk [DVD]), smart cards, flash memory devices (e.g., thumb drive, stick, key drive, and SD cards), and volatile and nonvolatile memory (e.g., RAM and ROM).

In the claims appended herein, the inventor invokes 35 U.S.C. §112, paragraph 6 only when the words "means for" or "steps for" are used in the claim. If such words are not used in a claim, then the inventor does not intend for the claim to be construed to cover the corresponding structure, material, or acts described herein (and equivalents thereof) in accordance with 35 U.S.C. §112, paragraph 6.

What is claimed is:

1. A patient monitoring system, comprising:
a main patient monitor configured to receive and collect one or more patient physiological parameters of a patient, and to provide an alarm in response, at least in part, to an alarm trigger, the alarm trigger including a determination that at least one of the collected patient physiological parameters has reached a predetermined value; and
a remote patient monitor having a band and an alarm reset configured to terminate the alarm, the remote patient monitor being configured to be worn by a caregiver, and further configured to receive a signal from the main patient monitor in response to the alarm and to transmit an indication about the alarm trigger, the indication comprising one or more of a notification that the patient is being attended to, a request by the caregiver for additional help, or a message about resolution of the alarm trigger.

2. The patient monitoring system of claim 1, wherein the main patient monitor is further configured to transmit at least one of: the collected patient physiological parameter data, patient identification, location identification, device data concerning the remote patient monitor, device data concerning one or more medical probes or delivery devices connected to the main patient monitor, and caregiver messages.

3. The patient monitoring system of claim 1, wherein the remote patient monitor is further configured to display at least one of: the collected patient physiological parameter received from the main patient monitor, patient identification, location identification, device data concerning the remote patient monitor, device data concerning one or more medical probes or delivery devices connected to the main patient monitor, and caregiver messages.

4. The patient monitoring system of claim 1, wherein patient physiological parameter data includes at least one of: a heart rate, a blood pressure, an oxygen saturation, an end-tidal $CO_2$, or a respiration rate.

5. The patient monitoring system of claim 1, wherein the band is attachable to the caregiver's arm, wrist, neck, belt, or waist.

6. The patient monitoring system of claim 1, wherein the main patient monitor and remote patient monitor are coupled wirelessly through one or more networks.

7. The patient monitoring system of claim 1, wherein the remote patient monitor is further configured to, in response to the signal from the main patient monitor, commence an action selected from a group consisting of vibration output, visual output, and auditory output.

8. The patient monitoring system of claim 1, wherein the alarm trigger comprises an overall urgency alarm.

9. The patient monitoring system of claim 1, wherein the main patient monitor is a plurality of different main patient monitors, and wherein each main patient monitor of the plurality of different main patient monitors is configured to monitor an individual patient and provide alarm signals to one or more of the remote patient monitors.

10. A method that facilitates remotely monitoring a patient using a remote patient monitor configured to be worn by a user, the method comprising:
receiving patient physiological parameter data at the remote patient monitor;
displaying the patient physiological parameter data on the remote patient monitor;
initiating a vibration alarm at the remote patient monitor in response to a received alarm trigger;
receiving at the remote patient monitor an alarm reset signal from the user;
receiving an alarm reset input at the remote patient monitor to terminate the alarm; and
transmitting an indication about the alarm trigger, the indication comprising one or more of a notification that the patient is being attended to, a request by the user for additional help, or a message about resolution of the alarm trigger.

11. The method of claim 10, wherein the alarm trigger comprises one or more of a general urgency alarm or an indication that a patient physiological parameter reached a predetermined value.

12. The method of claim 11, further comprising escalating an intensity of the vibration alarm, the intensity being indicative of a risk to a patient.

13. The method of claim 10, wherein receiving patient physiological parameter data includes receiving at least one of: a heart rate, a blood pressure, an oxygen saturation, an end-tidal $CO_2$, or a respiration rate.

14. The method of claim 10, wherein receiving patient physiological parameter data includes receiving patient physiological parameter data from more than one patient.

15. An article comprising: a non-transitory storage medium, the storage medium having instructions stored thereon, wherein, when the instructions are executed by a remote patient monitor having a band, the remote patient monitor performs operations comprising:
receiving patient physiological parameter data at a wireless module of the remote patient monitor;
displaying the patient physiological parameter data;
initiating a vibration alarm at the remote patient monitor in response to a received alarm trigger;

stopping the vibration alarm in response to an alarm reset input at the remote patient monitor; and transmitting an indication about the alarm trigger, the indication comprising one or more of a notification that the patient is being attended to, a request by the user for additional help, or a message about resolution of the alarm trigger.

16. The article of claim 15, wherein the alarm trigger comprises one or more of a general urgency alarm or an indication that a patient physiological parameter reached a predetermined value.

17. The article of claim 15, wherein the received patient physiological parameter data includes one or more of: a heart rate, a blood pressure, an oxygen saturation, an end-tidal $CO_2$, or a respiration rate.

18. The article of claim 15, wherein the received patient physiological parameter data includes physiological parameter data from more than one patient.

19. The patient monitoring system of claim 6, wherein the one or more networks is as a cloud-based network.

20. The patient monitoring system of claim 7, wherein the remote monitor is configured to vary an intensity of the commenced action, the intensity of the commenced action being indicative of a risk to the patient.

* * * * *